United States Patent [19]

Borovian

[11] 4,454,146
[45] Jun. 12, 1984

[54] SYNERGISTIC PRESERVATIVE COMPOSITIONS

[75] Inventor: Gayle E. Borovian, Dover, N.J.

[73] Assignee: Lever Brothers Company, New York, N.Y.

[21] Appl. No.: 378,372

[22] Filed: May 14, 1982

[51] Int. Cl.³ ..................... A01N 41/02; A01N 43/80
[52] U.S. Cl. ..................................... 424/270; 424/303
[58] Field of Search ................................ 424/270, 303

[56] References Cited

U.S. PATENT DOCUMENTS

| | | | |
|---|---|---|---|
| 2,121,928 | 6/1938 | Peter ..................................... | 260/60 |
| 3,065,123 | 11/1963 | Hinton et al. ......................... | 162/161 |
| 3,761,488 | 9/1973 | Lewis et al. .......................... | 260/302 |
| 3,947,594 | 3/1976 | Randall ................................. | 424/303 |
| 3,958,928 | 5/1976 | Lala ...................................... | 8/25 |
| 4,105,431 | 8/1978 | Lewis et al. .......................... | 424/270 |
| 4,110,238 | 8/1978 | Lala ...................................... | 252/89 |
| 4,137,243 | 1/1979 | Farmer ................................. | 260/378 |
| 4,144,024 | 3/1979 | Lala ...................................... | 8/25 |
| 4,252,694 | 2/1981 | Lewis et al. .......................... | 424/270 |

Primary Examiner—Allen J. Robinson
Attorney, Agent, or Firm—Milton L. Honig; James J. Farrell

[57] ABSTRACT

The present provides a preservative comprising:
(a) a first component selected from the group consisting of benzoic acid, formaldehyde, a mixture of 5-chloro-2-methyl-4-isothiazolin-3-one and 2-methyl-4-isothiazolin-3-one in a ratio of about 5:1 to 1:5, benzisothiazalone, and mixtures thereof; and
(b) a second component having the following formula:

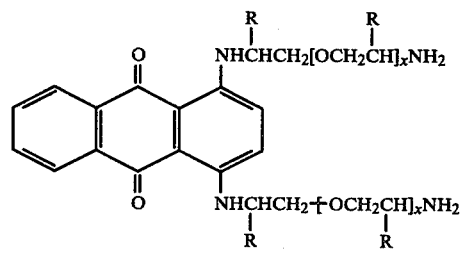

wherein x is about 2 to 33 and R is H or $CH_3$ and mixtures thereof;
wherein said second component is present in an amount at which said second component acts synergistically with said first component to kill or inhibit the growth of microorganisms.

The present invention also provides a preservative comprising:
(a) a first component selected from the group consisting of a mixture of 5-chloro-2-methyl-4-isothiazolin-3-one and 2-methyl-4-isothiazolin-3-one in a ratio of about 5:1 to 1:5, benzisothiazalone, and mixtures thereof; and a second component having the formula:

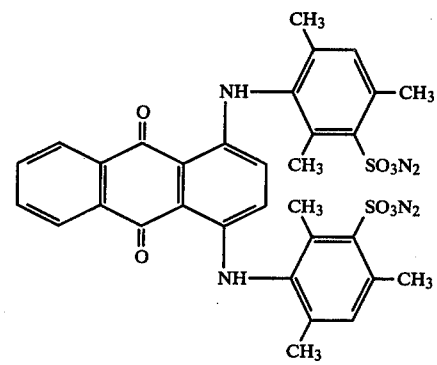

wherein said second component is present in an amount at which said second component acts synergistically with said first component to kill or inhibit the growth of microorganisms.

Additional embodiments of the invention include compositions comprising these preservatives as well as methods of using them.

24 Claims, No Drawings

SYNERGISTIC PRESERVATIVE COMPOSITIONS

The present invention is directed to preservatives, compositions containing preservatives, and methods for inhibiting the growth of microorganisms.

Many compositions are susceptible to contamination by microorganisms such as bacteria. Such compositions include, but are by no means limited to, personal care products such as shampoos, cosmetics, and soaps and household products such as laundry detergents, hard surface cleaners, fabric softeners and the like. In order to prevent these compositions from being contaminated by microorganisms, preservatives are frequently added to the formula. The contaminating microorganisms are, however, adaptable and, with time, often become immune to the preservative. Therefore, there is a continuing need for new preservatives which will inhibit the growth of microorganisms.

OBJECTS OF THE INVENTION

It is, therefore, an object of the present invention to provide a new preservative, compositions containing the new preservative, and methods for inhibiting the growth of microorganisms. A further object of this invention is to provide a preservative comprising two components which inhibit the growth of microorganisms synergistically in the presence of each other.

SUMMARY OF THE INVENTION

These and other objects as will become apparent to one of ordinary skill in the art have been attained by providing a preservative comprising:

(a) a first component selected from the group consisting of benzoic acid, formaldehyde, a mixture of 5-chloro-2-methyl-4-isothiazolin-3-one and 2-methyl-4-isothiazolin-3-one in a ratio of about 5:1 to 1:5, benzisothiazalone, and mixtures thereof; and (b) a second component having the following formula:

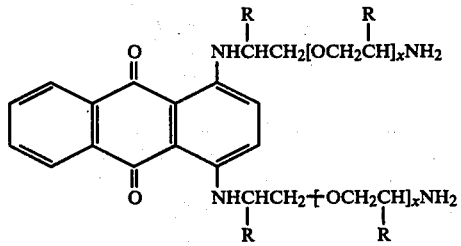

wherein x is about 2 to 33 and r is H or CH$_3$ and mixtures thereof;

wherein said second component is present in an amount at which said second component acts synergistically with said first component to kill or inhibit the growth of microorganisms.

In a second embodiment, the present invention provides a composition suitable for use as a personal care product or a household product, said composition being susceptible to contamination by microorganisms, comprising a preservative in an amount sufficient to kill or to inhibit the growth of said microorganisms wherein said preservative comprises:

(a) a first component selected from the group consisting of benzoic acid, formaldehyde, a mixture of 5-chloro-2-methyl-4-isothiazolin-3-one and 2-methyl-4-isothiazolin-3-one in a ratio of about 5:1 to 1:5, benzisothiazalone, and mixtures thereof; and (b) a second component having the following formula:

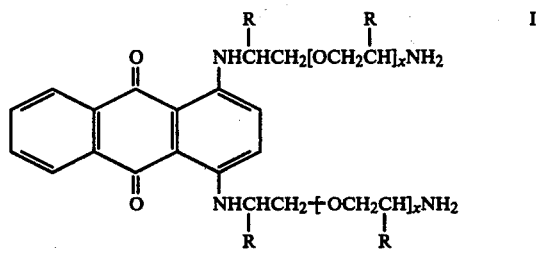

and mixtures thereof;

wherein said second component is present in an amount which acts synergistically with said first component to kill or inhibit the growth of microorganisms.

In a third embodiment, the present invention provides a method for killing or inhibiting the growth of microorganisms comprising contacting said microorganisms with a biocidal or biostatic amount of a compound having the formula:

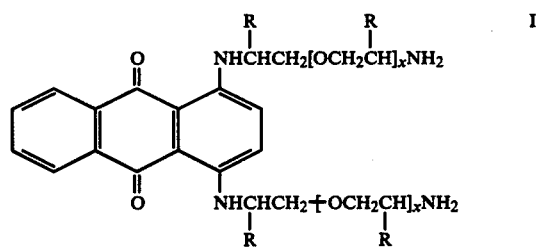

wherein x is about 2 to 33 and R represents hydrogen or methyl, or

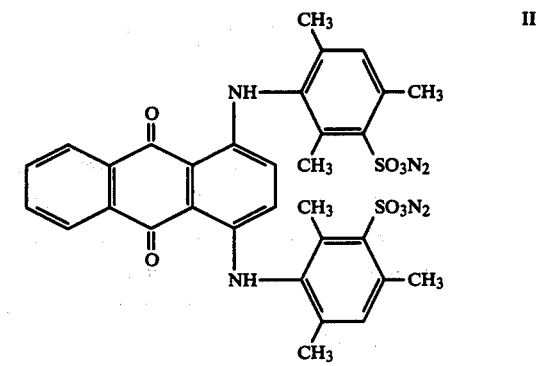

In a fourth embodiment, the present invention provides a method for killing or inhibiting the growth of microorganisms comprising contacting said microorganisms with a preservative comprising:

(a) a first component selected from the group consisting of benzoic acid, formaldehyde, a mixture of 5-chloro-2-methyl-4-isothiazolin-3-one and 2-methyl-4-isothiazolin-3-one in a ratio of about 5:1 to 1:5, benzisothiazalone, and mixtures thereof; and (b) a second component selected from the group of compounds having the following formula:

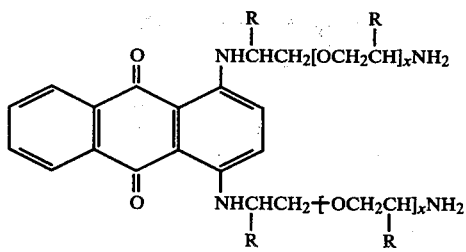

and mixtures thereof;

wherein said second component is present in an amount at which said second component acts synergistically with said first component to kill or inhibit the growth of microorganisms.

In a fifth embodiment, the present invention provides a preservative comprising:

(a) a first component selected from the group consisting of a mixture of 5-chloro-2-methyl-4-isothiazolin-3-one and 2-methyl-4-isothiazolin-3-one in a ratio of about 5:1 to 1:5, benzisothiazalone, and mixtures thereof; and (b) a second component having the formula:

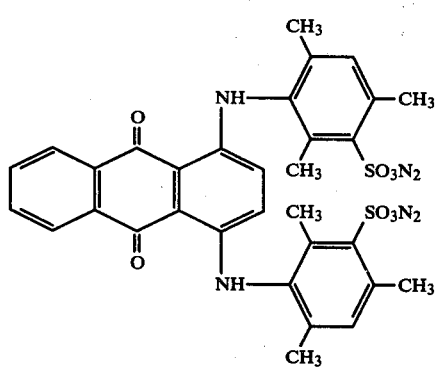

wherein said second component is present in an amount at which said second component acts synergistically with said first component to kill or inhibit the growth of microorganisms.

In a sixth embodiment, the present invention provides a composition suitable for use as a personal care product or a household product, said composition being susceptible to contamination by microorganisms, comprising a preservative in an amount sufficient to kill or inhibit the growth of said microorganisms wherein said preservative comprises:

(a) a mixture of 5-chloro-2-methyl-4-isothiazolin-3-one and 2-methyl-4-isothiazolin-3-one in a ratio of about 5:1 to 1:5, benzisothiazalone, or mixtures thereof; and (b) a second component having the formula:

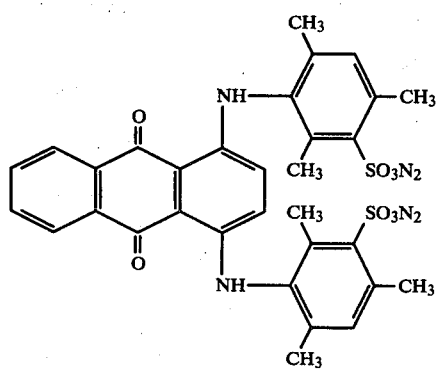

wherein said second component is present in an amount at which said second component acts synergistically with said first component to kill or inhibit the growth of microorganisms.

In a seventh embodiment, the present invention provides a method for killing or inhibiting the growth of microorganisms comprising contacting said microorganisms with a preservative comprising a first component selected from the group consisting of a mixture of 5-chloro-2-methyl-4-isothiazolin-3-one and 2-methyl-4-isothiazolin-3-one in a ratio of about 5:1 to 1:5, benzisothiazalone, and mixtures thereof and a second component having the formula:

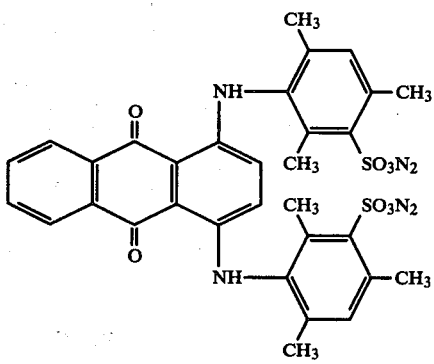

wherein said second component is present in an amount at which said second component acts synergistically with said first component to kill or inhibit the growth of microorganisms.

DETAILED DESCRIPTION OF THE INVENTION

In one embodiment, the present invention relates to a preservative. Preservatives are chemical components which either kill or inhibit the growth of microorganisms and, in particular, bacteria. Preservatives which kill microorganisms are said to be biocidal while those that inhibit the growth of microorganisms are said to be biostatic.

The bacteria of particular interest in the present invention are gram negative bacteria and, more particularly, those of the genus Pseudomonas. The preservatives presently claimed are especially effective against *Pseudomonas cepacia.*

The preservatives of the present invention comprise at least two components, herein called the first component and the second component. The first component comprises one or more traditional preservatives. Some suitable traditional preservatives include benzoic acid, sorbic acid, formaldehyde, gluteraldehyde, benzisothiazalone (A), and a mixture of 5-chloro-2-methyl-4-isothiazolin-3-one (B) and 2-methyl-4-isothiazolin-3-one (C) in a ratio of about 5:1 to 1:5, preferably 3 to 1. Compounds A, B and C have the following structures:

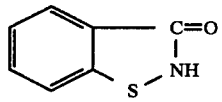

A

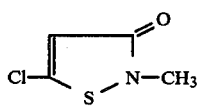

B

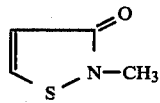

C

Compounds B and C in a ratio of about 3:1 are sold by Rohm and Haas under the trade names Kathon CG. Compound A is sold by ICI under the trade name Proxel.

The second component of the present invention comprises at least one compound which, in combination with the first component, kills or inhibits the microorganisms discussed above synergistically. The second component may or may not be biocidal or biostatic when used by itself. In the presence of the second compound, the first compound is biocidal or biostatic at lower concentrations than in the absence of the second compound.

Some suitable second compounds include dyes having the following formulas:

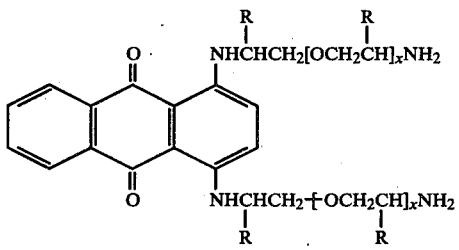

I wherein x is about 2 to 33, preferably about 5 to 33 and most preferably about 16 to 33 and R represents hydrogen or methyl, preferably methyl. This formula will be referred to as I in this application; and

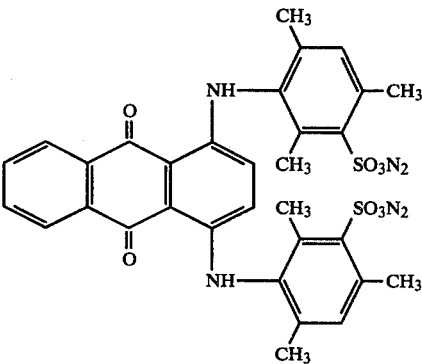

II

This compound will be referred to as II in this application.

The preferred second compound is I wherein x is about 33 and R is methyl. The compounds having Formula I are blue dyes described in U.S. Pat. No. 4,137,243 to Farmer and assigned to the Milliken Research Corporation. These compounds may be prepared by treating quinizarin in water with sodium hydroxide and sodium hydrosulfite. The resulting leucoquinizarin is treated with two moles of a polyoxyethylenediamine or a polyoxypropylenediamine. The later diamines are available from the Jefferson Chemical Company under the trade name Jeffamine. The resulting product is oxidized with air. The conditions for these reactions are described in the Farmer patent in Example 2, which is incorporated herein by reference.

II may be prepared by condensing one mole of 1,4-dichloroanthraquinone with 2 moles of mesidine sulfonate and converting the resulting product to the sodium salt. The structure of mesidine is 2,4,6-trimethyl-3-aminobenzenesulfonate.

Compound II is described in U.S. Pat. No. 2,121,928. The description of DPI and the method of its manufacture described in U.S. Pat. No. 2,121,928 is incorporated herein by reference.

The amount of the second compound in the preservative composition is that amount which interacts synergistically with the first compound to kill or inhibit the growth of microorganisms. Generally, the weight ratio of the second compound to the first compound will be 1000:1 to 1:10, preferably 100:1 to 1:5, and most preferably 10:1 to 1:1.

In a second embodiment of the present invention, the preservatives are present in compositions which are susceptible to degradation due to microorganisms. Suitable compositions include any composition in which preservatives may safely be used. Some suitable compositions include personal care products and household products. Some suitable personal care products include shampoos, hair conditioners, skin creams, suntan lotions and soaps. Some suitable household products include laundry detergents, dishwashing detergents, hard surface cleaners and fabric softeners.

The amount of the preservative in the composition is that amount which effectively inhibits the growth of the contaminating microorganism. The actual amount depends upon numerous factors. For example, one factor is the length of time the composition is to be stored. The longer the storage period, the higher the concentration of preservative. Moreover, the concentration of the preservative is a function of the particular first component and second component combination used, of the particular microorganism to be killed or inhibited, and the particular medium in which the microorganism is growing, as well as other variables. Generally, the total preservative will be present in the composition in amounts from about 0.02 to 1% by weight, preferably 0.05 to 0.5% by weight and most preferably 0.075 to 0.125% by weight.

A third embodiment of the present invention is a method for killing or inhibiting the growth of microorganisms. It has been discovered that the second components described above unexpectedly inhibit the growth of the microorganisms described above. It is desirable, of course, to add one of the first components to the second component in order to take advantage of the synergistic effect. The preferred second component is I. The preferred synergistic combination is I and a mixture of B and C in a ratio of about 3 to 1.

The present invention is operative at any pH. Where benzoic acid is used, the pH must be less than 7, preferably less than 5.5 and most preferably less than 4 to ensure that dissociation of the benzoic acid does not occur.

Having generally described the invention, a more complete understanding can be obtained by reference to certain specific examples, which are provided herein for purposes of illustration only and are not intended to limit the scope of the claimed invention unless otherwise specified.

EXAMPLES

Example 1

Fabric Softener

| Ingredients | % Active |
| --- | --- |
| Complex reaction product of two moles of an acid having the formula $R_1COOH$ wherein $R_1$ is an aliphatic hydrocarbon group containing from 15 to 19 carbon atoms and an alkaline diamine of the formula $H_2N-R_2-NR_3H$ wherein $R_2$ is an alkaline group containing from 1 to 2 carbon atoms and $R_3$ is a hydroxyalkyl group containing from 1 to 3 carbon atoms | 2.530 |
| Di(hydrogenated tallow)dimethyl-ammonium Chloride | 2.910 |
| Dicocodimethylammonium Chloride | 0.590 |
| Neodol 25-9$^a$ | 0.250 |
| Citric acid | 0.243 |
| Sodium Citrate | 0.012 |
| 4,4'-bis(2-phenolamino-4-diethanol-amine)-1,3,5-triazyl(6)diaminostilbene-2,2'-disulfonic acid* | 0.144 |
| Benzoic acid | 0.06 |
| I(x = ca.33, R = methyl) | 0.06 |
| $H_2O$ & miscellaneous | to 100% |

$^a$$C_{12}$ to $C_{15}$ fatty alcohols ethoxylated with 9 moles of ethylene oxide.
*Sold by Mobay and manufactured by Ciba-Geigy as Tinopal UNPA and Hilton Davis as Hiltamine Arctic Wite CWD

Comparative Example A

Fabric Softener

| Ingredients | % Active |
| --- | --- |
| Complex reaction product of two moles of an acid having the formula $R_1COOH$ wherein $R_1$ is an aliphatic hydrocarbon group containing from 15 to 19 carbon atoms and an alkaline diamine of the formula $H_2N-R_2-NR_3H$ wherein $R_2$ is an alkaline group containing from 1 to 2 carbon atoms and $R_3$ is a hydroxyalkyl group containing from 1 to 3 carbon atoms | 2.530 |
| Di(hydrogenated tallow)dimethyl-ammonium Chloride | 2.910 |
| Dicocodimethylammonium Chloride | 0.590 |
| Neodol 25-9$^a$ | 0.250 |
| Citric acid | 0.243 |
| Sodium Citrate | 0.012 |
| 4,4'-bis(2-phenolamino-4-diethanol-amine)-1,3,5-triazyl(6)diaminostilbene-2,2'-disulfonic acid* | 0.144 |
| II | 0.0035 |
| $H_2O$ & miscellaneous | to 100% |

$^a$$C_{12}$ to $C_{15}$ fatty alcohols ethoxylated with 9 moles of ethylene oxide.
*Sold by Mobay and manufactured by Ciba-Geigy as Tinopal UNPA and Hilton Davis as Hiltamine Arctic Wite CWD

Comparative Example B

Fabric Softener

| Ingredients | % Active |
| --- | --- |
| Complex reaction product of two moles of an acid having the formula $R_1COOH$ wherein $R_1$ is an aliphatic hydrocarbon group containing from 15 to 19 carbon atoms and an alkaline diamine of the formula $H_2N-R_2-NR_3H$ wherein $R_2$ is an alkaline group containing from 1 to 2 carbon atoms and $R_3$ is a hydroxyalkyl group containing from 1 to 3 carbon atoms | 2.530 |
| Di(hydrogenated tallow)dimethyl-ammonium Chloride | 2.910 |
| Dicocodimethylammonium Chloride | 0.590 |
| Neodol 25-9$^a$ | 0.250 |
| Citric acid | 0.243 |
| Sodium Citrate | 0.012 |
| 4,4'-bis(2-phenolamino-4-diethanol-amine)-1,3,5-triazyl(6)diaminostilbene-2,2'-disulfonic acid* | 0.144 |
| Formalin | 0.06 |
| II | 0.0035 |
| $H_2O$ & miscellaneous | to 100% |

$^a$$C_{12}$ to $C_{15}$ fatty alcohols ethoxylated with 9 moles of ethylene oxide.
*Sold by Mobay and manufactured by Ciba-Geigy as Tinopal UNPA and Hilton Davis as Hiltamine Arctic Wite CWD

Comparative Example C

Fabric Softener

| Ingredients | % Active |
| --- | --- |
| Complex reaction product of two moles of an acid having the formula $R_1COOH$ wherein $R_1$ is an aliphatic hydrocarbon group containing from 15 to 19 carbon atoms and an alkaline diamine of the formula $H_2N-R_2-NR_3H$ wherein $R_2$ is an alkaline group containing from 1 to 2 carbon atoms and $R_3$ is a hydroxyalkyl group containing from 1 to 3 carbon atoms | 2.530 |
| Di(hydrogenated tallow)dimethyl-ammonium Chloride | 2.910 |
| Dicocodimethylammonium Chloride | 0.590 |
| Neodol 24-9$^a$ | 0.250 |
| Citric acid | 0.243 |

-continued

| Ingredients | % Active |
|---|---|
| Sodium Citrate | 0.012 |
| 4,4'-bis(2-phenolamino-4-diethanol-amine)-1,3,5-triazyl(6)diaminostil-bene-2,2'-disulfonic acid* | 0.144 |
| Benzoic acid | 0.06 |
| II | 0.0035 |
| $H_2O$ miscellaneous | to 100% |

[a] $C_{12}$ to $C_{15}$ fatty alcohols ethoxylated with 9 moles of ethylene oxide.
*Sold by Mobay and manufactured by Ciba-Geigy as Tinopal UNPA and Hilton Davis as Hiltamine Arctic Wite CWD

Example 2
Method for Determining Preservative Activity

The Gradient Plate procedure was used to determine preservative activity as measured in "Minimum Inhibitory Concentration" (MIC) values. This method was described by Janet C. Curry in the 1965 CSMA Proceedings, 52nd Annual meeting. In accordance with this method, a square phage-type petrie dish was prepared so as to contain a base layer of acidified TSA (Difco's Tryptic Soy Ager, adjusted to pH 4 with citric acid) hardened in the form of a wedge. A top layer of acidified TSA containing a specific level of preservative component was hardened with the plate in a level position. A test agent in the top layer diffuses into the base layer causing a concentration gradient on the surface. Preservatives were prepared having gradient plate dilutions ranging from 1,000 to 0.5 ppm of the first component and from 1,500 to 500 ppm of the second component.

Twelve contaminated ($10^5$/ml) production samples and/or slant washings ($10^8$/ml, prepared from product contaminants carried on TSA slants) were then streaked across the surface of the ager using an apparatus which provides simultaneous and multiple inoculation. The plates were incubated at 32° C. for three days. The resulting growth streaks were measured in mm to the point of inhibition. The MIC values for a particular preservative or preservative component were determined by direct proportion of the gradient plate concentration of the preservative or preservative component to the growth front measurement.

Example 3
Preservative Activity of "Second Components"

The preservative activity of a number of "second components" was determined against Pseudomonas cepacia inocula grown on a medium described in Comparative Example A, Comparative Example B, Comparative Example C, and Example 1 by the gradient plate testing procedure described in Example 2. The results are shown in Table 1.

TABLE 1

ACTIVITY OF "SECOND COMPONENTS" BY GRADIENT PLATE TESTING

| Pseudomonas cepacia Inocula | Range of MIC Values in ppm Activities | | |
|---|---|---|---|
| | I(x = Ca.33) | II | Hexyl Carbitol |
| Comparative Example A | 375–510 | 375 | 700–1,000 |
| Washed Slants of Comparative Example A | 750–1,300 | 90–330 | 1,300–2,000 |
| Comparative Example B | 620–780 | 750->1,500 | 840–1,300 |
| Washed Slants of Comparative Example B | 550 | 570–1,200 | 1,300–1,800 |
| Comparative Example C | 620–830 | 750->1,500 | 740–1,400 |
| Washed Slants of Comparative Example C | 630–670 | 920–1,200 | 1,600–1,700 |
| Example 1 | 750–1,000 | 750 | 1,200–1,600 |
| Washed Slants of Example 1 | 1200–1,300 | 100–375 | 1,500–1,700 |

NOTE:
Three samples of each contaminated product-type (and product contaminant carried on TSA slants) were employed.

Compounds I and II and hexyl carbitol appear to be effective preservatives even when used by themselves.

Example 4

This example compares the activity of formaldehyde and benzoic acid toward Pseudomonas Cepacia grown in the formulas described in Comparatives Examples A, B and C as well as that described in Example 1. The method is that described in Example 2. The results are shown in Table 2.

TABLE 2

PRESERVATIVE ACTIVITY BY GRADIENT PLATE TESTING

| Pseudomona cepacia Inoculum | Range of MIC Values in ppm Active | |
|---|---|---|
| | Formaldehyde | Benzoic Acid |
| Comparative Example A (unpreserved) | 21–34 | 100–150 |
| Comparative Example B (contains formaldehyde) | 250–320 | 130–160 |
| Comparative Example C (contains benzoic acid) | 140–360 | 110–250 |
| Example 1 (contains benzoic acid and [DMC]) | 30–50 | 180–350 |

NOTE:
5 samples of each product type were employed.

Formaldehyde exhibited an MIC of about 30 ppm on the inocula from the unpreserved Comparative Example A. The inocula which had been grown in the presence of formaldehyde, i.e., in the formula of Comparative Example B, became more resistant to formaldehyde as evidenced by the relatively high MIC value of approximately 300 ppm.

Interestingly, benzoic acid also exhibited an MIC of approximately 300 ppm. Thus, the resistance to formaldehyde acquired by the bacteria which were grown in a medium containing formaldehyde was retained when the preservative was changed from formaldehyde to benzoic acid. This was not the case, however, when the formaldehyde resistant bacteria were treated with a combination of benzoic acid and I(x=Ca 33) as described in Example 1. This combination preservative in accordance with the present invention displayed an MIC of approximately 40 ppm. Unexpectedly, formaldehyde resistant bacteria are more susceptible to benzoic acid in the presence of I than in the absence of I.

Example 5
Preservative Activity of Benzoic Acid and Formaldehyde in combination with I Pseudomonas cepacia inocula from Comparative Examples A, B and C and Example 1 were grown on TSA slants. Inocula from washed slants of these examples were inoculated onto TSA containing 600 ppm I(x=ca.33, R=methyl), plus various levels of preservative. The procedure used was that described in Example 2. The results are shown in Table 3. The synergism displayed by the combination of I(x=ca.33, R=methyl) and benzoic acid and, to a lesser extent, that of I(x=ca.33, R=methyl) and formaldehyde is particularly apparent from the lower MIC values exhibited by benzoic acid and formaldehyde against the washed slants of Comparative Example A and Example 1.

Example 6

In the same way as Example 2, compound I(x=ca.33, R=methyl) and compound II in combination with benzoic acid and mixtures of B and C in a ratio of about 3:1 were tested for preservative activity against Pseudomonas cepacia from Comparative Example A and Pseudomonas aeruginosa at a pH of about 4. The results are shown in Table 4.

TABLE 3

| | Range of MIC Values in ppm Active | | | |
|---|---|---|---|---|
| *Pseudomonas cepacia* | Benzoic Acid | | Formaldehyde | |
| Inocula | TSA | TSA + I* | TSA | TSA + I* |
| Comparative Example A | 83–120 | Inhibited by DMC | 62 | Inhibited by DMC |
| Washed Slants of Comparative Example A | 160–210 | 11–33 | 52–62 | 19–28 |
| Comparative Example B | 62–97 | Inhibited by DMC | 250–330 | Inhibited by DMC |
| Washed Slants of Comparative Example B | 140–210 | Inhibited by DMC | 180–210 | Inhibited by DMC |
| Comparative Example C | 49–130 | Inhibited by DMC | 170–360 | Inhibited by DMC |
| Washed Slants of Comparative Example C | 130–220 | Inhibited by DMC | 200–210 | Inhibited by DMC |
| Example 1 | 130–220 | 21–87 | 42–62 | <10–35 |
| Washed Slants of Example 1 | 180–220 | 35–62 | 62 | 20–21 |

*x = ca.33, R = methyl

NOTE:
1. TSA + DMC: TSA prepared to contain 600 ppm DMC (Milliken Bluing Agent); adjusted to pH 4 with citric acid. Hexyl carbitol (DMC solvent) was also present at ~260 ppm level and, as shown in Table 1, is not considered to be active.
2. Control plates (without preservative) were included and several inocula were inhibited by the DMC present in TSA + DMC agar.
3. Three samples of each contaminated product-type (and product contaminant carried on TSA slants) were employed.

TABLE 4

GRADIENT PLATE RESULTS - MINIMUM INHIBITORY CONCENTRATIONS

| Compound (in agar) | P. cepacia | P. cepacia | P. cepacia | P. cepacia | P. aeruginosa |
|---|---|---|---|---|---|
| I | 210 | 375 | 750 | 750 | 230 |
| II | 190 | 190 | 375 | 375 | 375 |
| Benzoic acid | 125 | 125 | 70 | 125 | <31 |
| Mixture of B & C in a ratio of about 3:1 | 0.5 | 0.5 | 0.5 | 0.3 | <0.1 |
| 600 ppm I - Agar | | | | | |
| Benzoic Acid | | | | | |
| Mixture of B & C in a ratio of about 3:1 | | inhibited by 600 ppm I | | | |
| 500 ppm I - Agar | | | | | |
| Benzoic Acid | | inhibited by 500 ppm I | | | |
| 400 ppm I - Agar | | | | | |
| Benzoic Acid | <31 | inhibited by 400 ppm I | <31 | <31 | inhibited by 400 ppm I |
| Mixture of B & C in a ratio of about 3:1 | <0.1 | inhibited by 400 ppm I | <0.1 | <0.1 | inhibited by 400 ppm I |
| 300 ppm I - Agar | | | | | |
| Benzoic Acid | ~31 | ~31 | ~31 | ~31 | inhibited by 300 ppm I |
| 200 ppm I - Agar | | | | | |
| Benzoic Acid | ~31 | ~62 | 62 | ~62 | inhibited by 200 ppm I |
| Mixture of B & C in a ratio of about 3:1 | <0.1 | 0.2 | 0.1 | <0.1 | inhibited by 200 ppm I |
| 100 ppm I - Agar | | | | | |
| Benzoic Acid | ~31 | ~62 | 62 | ~62 | inhibited by 100 ppm I |
| 400 ppm II - Agar | | | | | |
| Benzoic Acid | | Inhibited | | | |
| 300 ppm II - Agar | | | | | |
| Benzoic Acid | | Inhibited | | | |
| 200 ppm II - Agar | | | | | |
| Benzoic acid | | Inhibited | | | |

TABLE 4-continued
GRADIENT PLATE RESULTS - MINIMUM INHIBITORY CONCENTRATIONS

| Compound (in agar) | P. cepacia | P. cepacia | P. cepacia | P. cepacia | P. aeruginosa |
|---|---|---|---|---|---|
| Mixture of B & C in a ratio of about 3:1 | | | Inhibited | | |
| 100 ppm II - Agar | | | | | |
| Benzoic acid | ~62 | ~62 | ~62 | inhibited | inhibited |
| Mixture of B & C in a ratio of about 3:1 | <0.1 | <0.1 | <0.1 | inhibited | inhibited |
| 50 ppm II - Agar | | | | | |
| Benzoic Acid | ~62 | ~62 | 62 | ~62 | inhibited |
| Mixture of B & C in a ratio of about 3:1 | <0.1 | <0.1 | <0.1 | <0.1 | inhibited |

The bacteria used in this example appears to be weaker than those used in Examples 3 to 5. The synergism between compounds I and II on the one hand and benzoic acid and a mixture of B and C on the other is apparent.

Examples 7 to 10

Shampoos containing preservatives according to this invention

TABLE 5

| | Percent by weight Example No. | | | |
|---|---|---|---|---|
| | 7 | 8 | 9 | 10 |
| Triethanolamine lauryl sulfate | 18.4 | 18.4 | 18.4 | 18.4 |
| Hydrogenated rosin | 10.0 | 5.0 | — | — |
| Polymerized rosin | — | — | 10.0 | 8.0 |
| Ethyl alcohol | 50.0 | 30.0 | — | — |
| Isopropyl alcohol | — | — | 40.0 | 40.0 |
| Perfume | 0.5 | 0.5 | 0.5 | 0.5 |
| I(R = H, x = 5) | .01 | — | — | — |
| Formaldehyde | .01 | 1.0 | — | — |
| I(R = CH$_3$, x = 33) | — | .06 | — | — |
| B + C (1:3) | — | — | 0.0005 | — |
| II | — | — | 0.5 | 0.5 |
| A | — | — | — | 0.01 |

Having now fully described the invention, it will be apparent to one of ordinary skill in the art that many changes and modifications can be made thereto without departing from the spirit or scope of the invention as set forth herein.

What is claimed is:

1. A preservative comprising:
   (a) a first component selected from the group consisting of a mixture of 5-chloro-2-methyl-4-isothiazolin-3-one and 2-methyl-4-isothiazolin-3-one in a ratio of about 5:1 to 1:5, benzisothiazalone, and mixtures thereof; and
   (b) a second component having the formula:

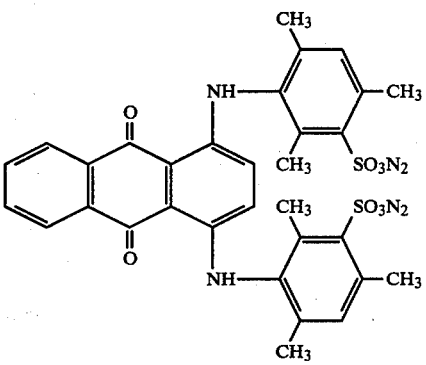

wherein the weight ratio of said second component to said first component is 1000:1 to 1:10, the combination acting to kill or inhibit the growth of bacteria.

2. A preservative according to claim 1 wherein the bacteria is a gram negative bacteria.

3. A preservative according to claim 1 wherein the bacteria is a bacteria of the genus Pseudomonas.

4. A preservative according to claim 3 wherein the bacteria is Pseudomonas cepacia.

5. A preservative according to claim 1 wherein said first component is a mixture of 5-chloro-2-methyl-4-isothiazolin-3-one and 2-methyl-4-isothiazolin-3-one in a ratio of 3 to 1.

6. A preservative according to claim 1 wherein the weight ratio of said second component to said first component is 100:1 to 1:5.

7. A preservative according to claim 1 wherein the weight ratio of said second component to said first component is 10:1 to 1:1.

8. A composition suitable for use as a personal care product or a household product, said composition being susceptible to contamination by bacteria, comprising:
   (i) a preservative wherein said preservative comprises:
      (a) a first component mixture of 5-chloro-2-methyl-4-isothiazolin-3-one and 2-methyl-4-isothiazolin-3-one in a ratio of about 5:1 to 1:5, benzisothiazalone, or mixtures thereof; and
      (b) a second component having the formula:

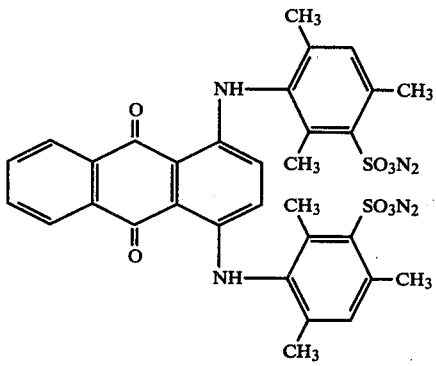

wherein the weight ratio of said second component to said first component is 1000:1 to 1:10, the combination acting to kill or inhibit the growth of bacteria; and (ii) a surface active agent selected from the group consisting of anionic, nonionic and cationic surfactants and mixtures thereof.

9. A composition according to claim 8 wherein the bacteria is a gram negative bacteria.

10. A composition according to claim 8 wherein the bacteria is a bacteria of the genus Pseudomonas.

11. A composition according to claim 10 wherein the bacteria is Pseudomonas cepacia.

12. A composition according to claim 8 wherein said first component is a mixture of 5-chloro-2-methyl-4-isothiazolin-3-one and 2-methyl-4-isothiazolin-3-one in a ratio of about 3 to 1.

13. A composition according to claim 8 wherein the weight ratio of said second component to said first component is 100:1 to 1:5.

14. A composition according to claim 8 wherein the weight ratio of said second component to said first component is 10:1 to 1:1.

15. A composition according to claim 8 wherein the preservative is present in an amount from about 0.02 to 1% by weight.

16. A composition according to claim 8 wherein the preservative is present in an amount from 0.05 to 0.5% by weight.

17. A composition according to claim 8 wherein the preservative is present in an amount from 0.075 to 0.125% by weight.

18. A method for killing or inhibiting the growth of bacteria comprising contacting said bacteria with a preservative comprising a first component selected from the group consisting of a mixture of 5-chloro-2-methyl-4-isothiazolin-3-one and 2-methyl-4-isothiazolin-3-one in a ratio of about 5:1 to 1:5 benzisothiazalone, and mixtures thereof and a second component having the formula:

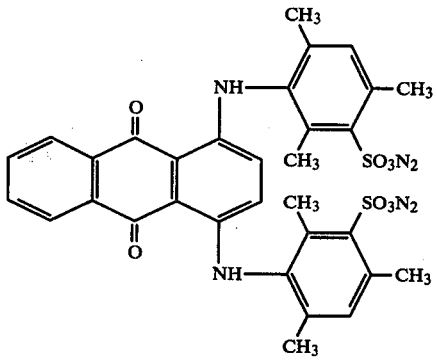

wherein the weight ratio of said second component to said first component is 1000:1 to 1:10, the combination acting to kill or inhibit the growth of bacteria.

19. A method according to claim 18 wherein the bacteria is a gram negative bacteria.

20. A method according to claim 18 wherein the bacteria is a bacteria of the genus Pseudomonas.

21. A method according to claim 20 wherein the bacterial is Pseudomonas cepacia.

22. A method according to claim 18 wherein the first component is a mixture of 5-chloro-2-methyl-4-isothiazolin-3-one and 2-methyl-4-isothiazolin-3-one in a ratio of about 3 to 1.

23. A method according to claim 18 wherein the weight ratio of said second component to said first component is 100:1 to 1:5.

24. A method according to claim 18 wherein the weight ratio of said second component to said first component is 10:1 to 1:1.

* * * * *